United States Patent [19]

Rogers et al.

[11] Patent Number: 4,838,281
[45] Date of Patent: * Jun. 13, 1989

[54] LINEAR SUCTION CONTROL SYSTEM

[75] Inventors: Wayne W. Rogers, Napa; Carl C. T. Wang, Piedmont, both of Calif.

[73] Assignee: Alcon Laboratories, Inc., Fort Worth, Tex.

[*] Notice: The portion of the term of this patent subsequent to Nov. 17, 2004 has been disclaimed.

[21] Appl. No.: 107,971

[22] Filed: Oct. 13, 1987

Related U.S. Application Data

[63] Continuation of Ser. No. 706,654, Feb. 28, 1989, Pat. No. 4,706,687.

[51] Int. Cl.⁴ .......................................... A61M 13/00
[52] U.S. Cl. ..................................... 128/752; 604/51; 604/65; 604/119
[58] Field of Search ...................... 128/749, 752–755, 128/758; 604/35, 51, 65, 118–119; 137/902, 907, 909, 526

[56] References Cited

U.S. PATENT DOCUMENTS

| | | |
|---|---|---|
| Re. 23,496 | 5/1952 | Seeler . |
| 1,847,658 | 3/1932 | Lasker . |
| 3,033,196 | 5/1962 | Hay . |
| 3,252,623 | 5/1966 | Corbin . |
| 3,266,494 | 8/1966 | Brownrigg . |
| 3,399,677 | 9/1968 | Gould . |
| 3,561,429 | 2/1971 | Hewett . |
| 3,624,821 | 11/1971 | Henderson . |
| 3,693,613 | 9/1972 | Kelman . |
| 3,752,161 | 8/1973 | Bent . |
| 3,763,862 | 10/1973 | Spieth . |
| 3,815,604 | 6/1974 | O'Malley . |
| 3,842,839 | 10/1974 | Malis . |

(List continued on next page.)

FOREIGN PATENT DOCUMENTS

| | | |
|---|---|---|
| 2547185 | 4/1977 | Fed. Rep. of Germany ... 128/303 R |
| 2549727 | 2/1985 | France . |

OTHER PUBLICATIONS

United Surgical Corporation brochure on "Phacotron Plus", one page.
Surgical Design Company brochure on Keats "Ultrasonic I/E Mini Probe" by A. Banko, 2 pages.
Surgical Design Corporation brochure on U.S. Phaco System, 1 page.
Coopervision brochure on System VI, 1 page.
Coopervision brochure on Cavitron/Kelman Model 6500 EIS and Model 7500, 6 pages.
Surgical Design brochure on "The Ocusystem", 1 page.
Coopervision brochure on "Cavitron/Kelman Phaco--Emulsifier Aspirator" Model 8001, 2 pages.
Coopervision brochure on Cavitron/Kelman Phaco--Emulsifier Aspirator Model 9001, 6 pages.
Greishaber of Switzerland brochure on "MPC, the Membrane Peeler Cutter", 5 pages.
Site TXR Product catalog, 21 pages.
Parks, "Intracapsular Asoiration" article, pp. 59–74.
Van Oldenborgh, "Correction of Late Operative Com-
(List continued on next page.)

Primary Examiner—Kyle L. Howell
Assistant Examiner—Angela D. Sykes
Attorney, Agent, or Firm—Zarley McKee, Thomte, Voorhees & Sease

[57] ABSTRACT

A linear suction control system 10 includes a linear solenoid valve 11 which exhibits a flow through rate having a known proportional relationship with the current through the solenoid 30. Regulated fluid pressure 12 is fed through the linear solenoid valve 11 to a venturi-type pressure vacuum converter 17. The resulting vacuum is proportional to the flow rate through the valve 11 and thus to the current through the solenoid 30. A transducer 16 samples the vacuum output and produces a signal fed to a differential amplifier 17. The signal is compared in negative feedback fashion with a variable input voltage set by a potentiometer 18 or other variable voltage source, so that the transducer signal tracks the voltage source signal. The voltage source can comprise a potentiometer 18 actuated by a foot switch 19 or the like, so that angular position of the foot switch 19 relates directly and predictably to the vacuum output of the converter 13. The linear solenoid valve 11 includes an electromagnetic coil 30 arranged to translate a valve member 36, with an elastic member 35 biasing the valve member closed with a generally linear restoring force.

23 Claims, 1 Drawing Sheet

U.S. PATENT DOCUMENTS

| | | |
|---|---|---|
| 3,884,238 | 5/1975 | O'Malley . |
| 3,899,829 | 8/1975 | Storm . |
| 3,903,881 | 9/1975 | Weigl . |
| 3,913,584 | 10/1975 | Walche . |
| 3,920,014 | 11/1975 | Banko . |
| 3,930,505 | 1/1976 | Wallach . |
| 3,977,425 | 8/1976 | Hayashida . |
| 3,982,539 | 9/1976 | Muriot . |
| 4,004,590 | 1/1977 | Muriot . |
| 4,135,515 | 1/1979 | Muriot . |
| 4,178,707 | 9/1979 | Douvas . |
| 4,204,328 | 5/1980 | Kutner . |
| 4,217,993 | 8/1980 | Jess . |
| 4,223,676 | 9/1980 | Wuchinich . |
| 4,245,815 | 1/1981 | Willis . |
| 4,308,385 | 1/1982 | Abbey . |
| 4,314,560 | 2/1982 | Helfgott . |
| 4,320,761 | 3/1982 | Haddad . |
| 4,354,838 | 10/1982 | Hoyer . |
| 4,395,258 | 7/1983 | Wang . |
| 4,396,386 | 8/1983 | Kurtz . |
| 4,445,517 | 5/1984 | Feild . |
| 4,474,411 | 6/1981 | Dotson, Jr. . |
| 4,475,904 | 10/1984 | Wang . |
| 4,493,695 | 1/1985 | Cook . |
| 4,493,698 | 1/1985 | Wang . |
| 4,522,371 | 6/1985 | Fox . |
| 4,524,948 | 6/1985 | Hall . |
| 4,530,357 | 7/1985 | Pawlowski . |
| 4,540,406 | 9/1985 | Miles . |
| 4,598,729 | 7/1986 | Naito . |

OTHER PUBLICATIONS plications by Means of a Suction Cutter," Ophthal. Soc. U.K. (1980), 100, 219, pp. 219-221.

Helfgott, "A System for Variable Aspiration of Material Dissected from the Posterior Chamber", Ophthalmic Surgery, vol. 15, Jun. 1984, pp. 529-530.

Charles and Wang, "A Linear Suction Control for the Vitreous Cutter (Ocutome)", Arch. Ophthalmol., vol. 99, Sep. 1981, p. 1631.

Crosby, "On Control of Artificial Hearts", pp. 89-114.

Mrava, Cardiac Engineering, vol. 3, pp. 31-68, 1970.

Micro-Vit Vitrectomy System Product brochure and instruction manual.

Storz Irrigation Aspiration System product brochure and instruction manual.

Hayashi et al.; "Japanese Experience with Ventricular Assist Devices"; *IEEE Engr. in Med. and Biol.*, 3-1986, pp. 30-36.

Greishaber and Co. of Switzerland; "*Sutherland Rotatable Intraocular Microscissors*" product brochure-2 pages.

Murayama et al.; "A Portable Air Driving Unit for Blood Pumps", *Japanese Journal of Artificial Organs*, vol. 14, No. 3, 7-1985, pp. 1206-1209.

Scuderi et al.; "La Chirurgie de la Cataracte Congenitale"; pp. 174-185.

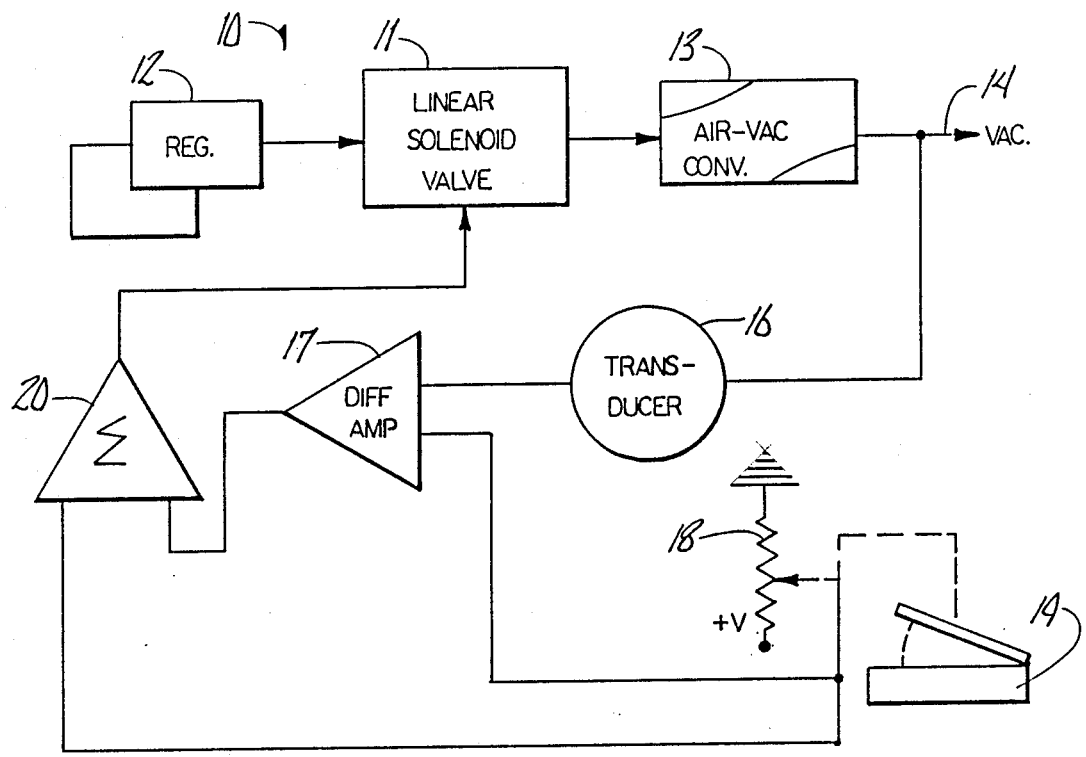
Fig. 1
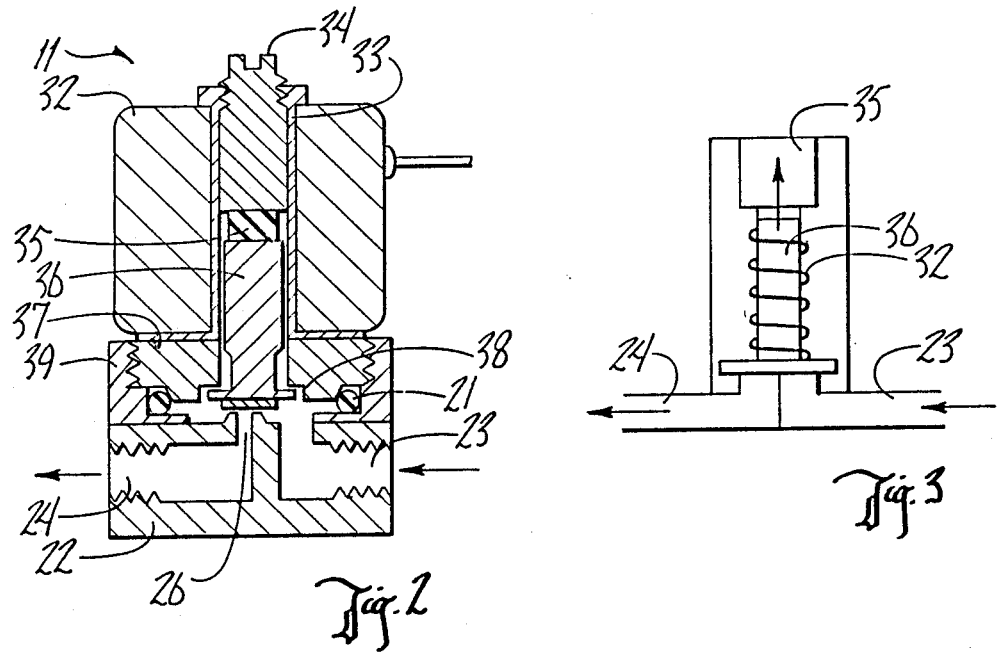
Fig. 2
Fig. 3

LINEAR SUCTION CONTROL SYSTEM

This is a divisional of co-pending application Ser. No. 706,654 filed on 2-28-85, now U.S. Pat. No. 4,706,687.

BACKGROUND OF THE INVENTION

In the field of surgery as well as in many other technical disciplines there is a great need for a suction system in which the vacuum or negative pressure level can be highly controlled. In ophthalmic surgery, for example, many cutting instruments draw the tissue into the cutting edges by the use of suction. Indeed, the tissue removal rate is effectively controlled by the suction effect which is related directly to the negative pressure level. Thus controlling the negative pressure level to a fine degree is highly desirable to provide to the surgeon a concomitant degree of control of the tissue removal process.

However, prior art suction systems are generally deficient in their poor control of the vacuum level. Many systems employ a pressure delivery tank in which the vacuum level is controlled by selective connection to a lower pressure source or to a selectively valved "leak" from atmospheric pressure. These systems are characteristically underdamped pressure oscillators, in that the negative pressure level often swings wildly about the desired (and often changing) level. Furthermore, purposely introducing a leak into a vacuum system is inherently wasteful, and contradicts sound engineering practice. Also, the large volume of most systems causes a delay in their response, which may lead to poor user control and overshooting of the desired vacuum level.

Some suction systems deliver vacuum to a surgical handpiece, and provide a series of leak ports adapted to be blocked or unblocked by one or more of the fingers of the hand wielding the handpiece. The surgeon may slide a finger along the row of ports to unblock ports and thus set a limited number of vacuum suction levels. This pressure control is not continuous, being limited to a few discrete levels, and even these levels can be set only within a broad range. Here again, introducing a series of leaks is inherently inefficient and wasteful.

SUMMARY OF THE PRESENT INVENTION

The present invention generally comprises a vacuum or negative pressure delivery system which features precise, continuously variable, predictable control of the vacuum delivered. A significant feature is that the variation in vacuum may be adjusted electronically to follow any desirable functional mathematical relationship to a control signal. For example, the system may be arranged so that the vacuum level will vary linearly with respect to the position of a control lever, pedal, or the like. The vacuum does not fluctuate wildly, and the vacuum at any position of the control lever or pedal is predictable and reproducible. The system may be adapted to surgical suction/evacuation systems and the like, as well as to other technical disciplines.

The linear suction control system includes a linear solenoid valve which exhibits a flow through rate which varies with respect to the current through the solenoid in a known manner. Regulated fluid pressure is fed through the linear solenoid valve to a venturi-type pressure vacuum converter. The resulting vacuum is proportional to the flow rate through the valve and thus to a function of the current through the solenoid. A transducer samples the vacuum output and produces a signal fed to a differential amplifier. The signal is compared with a variable input voltage set by a potentiometer or other variable voltage source in negative feedback fashion, so that the transducer signal tracks the voltage source signal by actuating the valve to correct the flow rate so that the desired pressure will be attained. The voltage source may comprise a potentiometer actuated by a foot switch or the like, so that angular position of the foot switch relates directly and predictably to the vacuum output. The linear solenoid valve includes an electromagnetic coil arranged to drive a valve member, with an elastic member biasing the valve member closed with a generally linear restoring force. The circuitry of the differential amplifier may be arranged so that the overall relationship of the vacuum level to the controller position may follow any desired function. Thus the response to a control device may be tailored to suit the user, the process to which the vacuum is applied, or the like.

BRIEF DESCRIPTION OF THE DRAWINGS

FIG. 1 is a functional block diagram of the vacuum control and delivery system of the present invention.

FIG. 2 is a cross-sectional elevation of the linear solenoid valve according to the present invention.

FIG. 3 is a schematic represenation of the linear solenoid valve depicted in FIG. 2.

DESCRIPTION OF THE PREFERRED EMBODIMENT

The present invention generally comprises a vacuum (negative gauge pressure) delivery system which features fine control of the vacuum which is generated and delivered. With reference to FIG. 1, the system includes a novel linear solenoid valve 11. The linear solenoid valve is an electrically actuated valve which exhibits a through-flow rate proportional to the current through the solenoid coil, as will be explained in the following. A regulated fluid pressure supply 12 is fed through the linear solenoid valve 11 to a converter 13 which converts positive fluid pressure to a corresponding vacuum (negative pressure). One such device, manufactured by Air-Vac Co., utilizes a venturi restriction in the flow path of the pressurized fluid to generate a partial vacuum. The partial vacuum (negative gauge pressure) is proportional to the flow rate of the pressurized fluid through the converter 13. The resulting partial vacuum output 14 may be connected to any device requiring negative pressure, such as a surgical cutting device, suction/evacuation device, or the like.

A transducer 16 is connected to the output 14 to sample the negative pressure level of the output. The transducer 16 generates a signal which is fed to a differential amplifier 17. The differential amplifier 17 is also fed a reference signal generated by a variable voltage device, such as the potentiometer 18. The potentiometer is actuated by a control device, such as a foot pedal controller 19 having a continuously variable range of angular position settings which are directly related to the potentiometer setting. It may be appreciated that other reference voltage sources may be employed, such as a microprocessor system in which the pedal position of the device 19 is read by a linear shaft position encoder, and the pedal position is correlated with the desired voltage level by a look-up table stored in the system memory.

The differential amplifier 17 is configured to compare the transducer signal with the reference voltage level, and to produce a difference output which is provided to adder 20. Further the original reference voltage signal from foot pedal controller 19 is provided to adder 20. These two signals are added together by adder 20 and drive the linear solenoid valve in typical feedback loop fashion. If the signal from transducer 16 is different from that from controller 19, the difference will be combined with the signal from controller 19 to cause the vacuum at output 14 to track the level set by controller 19. If the difference between the signals provided to differential amplifier 17 is zero, only the signal from controller 19 is provided to adder 20 and the vacuum output at 14 is at the desired level set by controller 19. Due to the fact that the relationship between the flow rate through the valve 11 varies in generally linear proportion to the current through the solenoid of valve 11, and that the partial vacuum output level from the converter is related directly to the flow rate therethrough, the differential amplifier circuitry is configured to produce a system in which the vacuum level is directly related to the position of the pedal of the controller 19. This overall system response may be configured as linear, in which incremental change in pedal position divided by incremental change in negative pressure level results in a constant number. On the other hand, the system of the present invention may be configured to have a particular non-linear response, as may be required by the end user of the system.

It should be noted that the negative pressure delivery system of the present invention does not employ the standard pressure accumulator tank, and thus has no large volumes which typically slow the response of a partial vacuum system. Thus the prior art problem of overshooting the desired pressure level in reaching steady state in the accumulator tank is obviated.

With regard to FIGS. 2 and 3, the construction of the linear solenoid valve 11 includes a solenoid coil 32 wound about a hollow tubular member 33. One end of the tubular member 33 is sealed by a plug 34, and the stem of a valve member 36 is slidably received in the other end portion of the member 33. A significant feature of the invention is the provision of an elastic member 35 disposed between the plug 34 and the valve stem 36 to bias the latter member outwardly of the tube 33. The member 35 may comprise elastomeric rubber, foamed plastic, or the like, and it exhibits a restoring force which varies linearly with the amount of compression applied thereto.

A valve head member 37 is secured at the open end of the tube 33, and includes a valve seat 38 adapted to receive the distal end of the valve stem 36. A collar 39 is secured to the member 37 by threads, and an O-rinq seal 21 retains pressure in the assembly. A valve port member 22 is joined to the collar, and includes an inlet port 23 and an outlet port 24. The flow path between the inlet and outlet includes an orifice 26 which is selectively and variably opened by the valve member 36. The magnetic force generated by the solenoid coil 32 drives the valve stem 36 toward the plug 34, thus opening the orifice 26. However, this translation is opposed by linear restoring force of the elastic member 35, so that an incremental increase in the fluid flow through the orifice 26 requires an incremental increase in the magnetic force driving the valve stem and thus in the current fed through the coil 32. The elastic member also provides a damping effect to the motion of the valve stem, and thus is superior to a metal spring or the like. The material of the elastic member is generally serviceable through approximately one billion operating cycles.

We claim:

1. A surgical suction control system for aspirating and cutting tissue comprising:
   valve means for regulating the flow of pressurized fluid; means for converting the pressurized fluid into a vacuum,
   which converting means is adapted to communicate with a device for aspirating and cutting tissue; transducer means for sensing the vacuum and for generating
   a first signal in response thereto; adjustable controller means for selecting an appropriate vacuum
   level for aspirating and cutting tissue and for generating, in response to adjustment of the controller means, a p1 second signal which corresponds to said level; comparator means for comparing the first and second signals and
   generating a third signal to drive the valve means to regulate the flow of pressurized fluid and the vacuum in order to regulate the aspirating and cutting of tissue.

2. The suction control system of claim 1 wherein said valve means includes;
   a valve port adapted to allow the flow of pressurized fluid therethrough;
   a valve stem means for selectively controlling the size of the valve port;
   an elastic member disposed to resiliently bias said valve stem means to close said valve port;
   solenoid means responsive to said third signal for urging said valve stem means against said elastic member to open said valve port.

3. The surgical suction control system of claim 1 wherein said comparator means generates said third signal according to a predetermined function.

4. The surgical suction control system of claim 3 wherein the function of the comparator means is generally linear.

5. The surgical suction control system of claim 3 wherein the function of the comparator means is non-linear.

6. The surgical suction control system of claim 1 wherein the comparator means comprises a feedback circuit comparing the signals from the transducer means and the controller means and generating a third signal to cause the suction control system to generally follow the signal from the controller means.

7. The surgical suction control system of claim 6 wherein the comparator means sends an increasing signal to the valve means upon corresponding selection of the controller means, sends a decreasing signal to the valve means upon a selected signal from the controller means, and maintains a desired signal to the valve means upon a selected corresponding signal of the controller means.

8. The surgical suction control system of claim 1 wherein the comparator means comprises a differential amplifier to which is input said first signal representing current vacuum level and said second signal representing a reference signal from the controller means; and a summing amplifier to which is input the differential output of the differential amplifier and the reference signal of the controller means; so that the output of the summing amplifier follows the selected control of the controller means and sends a signal to a solenoid valve means correspondingly.

9. A suction control system comprising:
a valve means for regulating the flow of a pressurized fluid;
means for converting the pressurized fluid into a vacuum; transducer means for sensing the vacuum and for generating a first signal in response thereto;
adjustable controller means for selecting an appropriate vacuum level and for generating, in response to adjustment of the controller means, a second signal which corresponds to said vacuum level;
comparator means for comparing the first and second signals and generating a third signal to drive the valve means to regulate the flow of pressurized fluid flow therethrough, to in turn regulate the vacuum.

10. The suction control system of claim 9 wherein said solenoid valve means includes:
a valve port adapted to allow the flow of pressurized fluid therethrough;
a valve stem means for selectively controlling the size of the valve port;
an elastic member disposed to resiliently bias said valve stem means to close said valve port;
solenoid means responsive to said third signal for urging said valve stem means against said elastic member to open said valve port.

11. A negative guage pressure delivery and control system including:
a valve means having a pressurized fluid flow rate therethrough which is proportional to an output signal;
pressure-vacuum converter means connected to receive said pressurized fluid through said valve and to generate a negative pressure level output proportional to said flow rate through said valve;
transducer means for sensing the negative pressure level and generating a transducer signal in response thereto;
variable reference signal source means for generating a selectively variable reference signal;
comparator means for comparing said transducer signal and said variable reference signal and generating an output signal representing the difference between said transducer signal and said variable reference signal, said output signal being connected to drive said valve to control the fluid flow rate and produce a negative pressure output proportional to said variable reference signal.

12. The negative gauge pressure delivery and control system of claim 11, wherein said pressure-vacuum converter means includes:
a venturi-type converter means for generating a negative gauge pressure from the flow of said fluid.

13. The negative gauge pressure delivery and control system of claim 11, wherein said valve means includes;
a valve port adapted to allow the flow of fluid therethrough;
a valve member disposed to selectively vary the fluid flow through said valve port;
an elastic member disposed to resiliently bias said valve member to close said valve port; and
solenoid means being disposed to translate said valve member against said resilient bias to open said valve port.

14. The negative gauge pressure delivery and control system of claim 13, wherein said elastic member is composed of an elastomeric rubber compound.

15. The negative gauge pressure delivery and control system of claim 11, wherein said reference signal source means includes a control device having a movable control element which varies said reference signal in accordance with the position thereof.

16. The negative gauge pressure delivery and control system of claim 15, wherein said comparator means includes means for adjusting the overall response of said system so that incremental change in the position of said control element bears a predetermined and reproducible incremental change in the negative pressure output of said converter means.

17. The negative gauge pressure delivery and control system of claim 16, wherein said overall response is a linear relationship between change in position of said control element and change in the level of said negative pressure output.

18. The negative gauge pressure delivery and control system of claim 15, wherein said control device comprises a pedal controller, and said control element comprises a pedal extending from said pedal controller and pivotally supported thereon.

19. A method for controlling a suction system for aspirating and cutting tissue in surgical applications comprising:
connecting a valve means between a source of positive pressurized fluid and a means for converting pressurized fluid flow to vacuum;
connecting a surgical tool utilizing vacuum to the output of the means for converting pressurized fluid flow to vacuum;
monitoring continuously the level of vacuum going to the surgical instrument;
producing a first signal corresponding to the vacuum level to the surgical instrument;
producing a second signal from an adjustable variable controller means, said second signal corresponding to the desired vacuum level to the surgical instrument in response to adjustment of the controller means;
comparing the instantaneous and contemporaneous first and second signals;
producing a third signal to drive the valve means which regulates the flow of pressurized fluid to the means for converting air to vacuum, the third signal corresponding to the comparison of the first and second signals.

20. The method of claim 19 wherein the valve means comprises a solenoid valve means.

21. The method of claim 20 wherein the third signal corresponds to increased current to the solenoid valve means when the first signal is less than the second signal, decreased current to the solenoid valve means when the first signal is greater than the second signal, and maintenance of current level to the solenoid valve means when the first signal is generally equivalent to the second signal.

22. An improved ophthalmic surgical instrument control system which provides direct and immediate linear responsiveness from a foot pedal depression to the surgical instrument for surgical control comprising:
solenoid valve means for proportional regulation of the flow of pressurized fluid;

means for converting the pressurized fluid into a vacuum, which communicates with a surgical instrument for aspirating and cutting tissue;

transducer means for sensing the vacuum and for generating a first signal in response thereto;

adjustable controller means for selecting an appropriate vacuum level for aspirating and cutting tissue and for generating, in response to adjustment of the controller means, a second signal which corresponds to said level;

comparator means for comparing the first and second signals and generating a third signal which drives the solenoid valve means for proportional regulation of the flow of pressurized fluid and proportional regulation of the vacuum to provide immediate responsiveness from foot pedal depression to the surgical instrument.

23. A method for improved control of an ophthalmic surgical suction system for aspirating and cutting tissue in ophthalmic surgical applications, which provides direct and immediate linear responsiveness from foot pedal depression to a surgical instrument for surgical control, comprising:

connecting a solenoid valve between a source of positive pressurized fluid and a means for proportionally converting pressurized fluid flow to vacuum;

connecting a surgical tool utilizing vacuum to the output of the means for proportionally converting pressurized fluid flow to vacuum;

monitoring continuously the level of vacuum at the surgical instrument;

producing a first signal corresponding to the vacuum level at the surgical instrument;

producing a second signal from a foot pedal including an adjustable variable controller means, said second signal corresponding to the desired vacuum level to the surgical instrument in response to adjustment of the controller means;

comparing the instantaneous and contemporaneous first and second signals;

producing a third signal which drives the solenoid valve for proportional regulation of the flow of pressurized fluid to the means for converting air to vacuum, and proportional regulation of the vacuum for direct and immediate responsiveness from foot pedal depression to the surgical instrument, the third signal corresponding to the comparison of the first and second signals.

* * * * *